(12) United States Patent
Feith

(10) Patent No.: US 11,383,073 B2
(45) Date of Patent: Jul. 12, 2022

(54) LUER HAVING TUBING RETENTION POCKET BOND

(71) Applicant: CareFusion 303, Inc., San Diego, CA (US)

(72) Inventor: Raymond Feith, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 553 days.

(21) Appl. No.: 16/009,813

(22) Filed: Jun. 15, 2018

(65) Prior Publication Data

US 2019/0381304 A1 Dec. 19, 2019

(51) Int. Cl.
*A61M 39/10* (2006.01)

(52) U.S. Cl.
CPC . *A61M 39/1011* (2013.01); *A61M 2039/1027* (2013.01); *A61M 2207/00* (2013.01)

(58) Field of Classification Search
CPC .............. A61M 39/10; A61M 39/1011; A61M 2039/1027; A61M 2039/1077; A61M 2207/00
See application file for complete search history.

(56) References Cited

U.S. PATENT DOCUMENTS

| | | | |
|---|---|---|---|
| 2010/0063482 A1 | 3/2010 | Mansour et al. | |
| 2013/0035668 A1* | 2/2013 | Kitani | A61M 39/26 604/535 |
| 2013/0345587 A1 | 12/2013 | Colman | |
| 2015/0247597 A1* | 9/2015 | Okiyama | A61M 39/045 285/317 |

FOREIGN PATENT DOCUMENTS

WO WO-2005049129 A1 6/2005

OTHER PUBLICATIONS

Written Opinion of the International Preliminary Examining Authority for Application No. PCT/US2019/036997, dated May 27, 2020, 7 pages.
International Preliminary Report on Patentability from the International Preliminary Examining Authority for Application No. PCT/US2019/036997, dated Sep. 2, 2020, 21 pages.
International Search Report and Written Opinion for Application No. PCT/US2019/036997, dated Aug. 9, 2019, 13 pages.

* cited by examiner

*Primary Examiner* — Nathan R Price
*Assistant Examiner* — Anh Bui
(74) *Attorney, Agent, or Firm* — Morgan, Lewis & Bockius LLP

(57) ABSTRACT

A connector comprises a body having a tubing portion and a luer portion axially opposite the tubing portion and connected thereto, an internal passageway defined by an inner circumferential surface of the connector, the passageway extending axially between the tubing portion and the luer portion and in fluid communication therewith, a stopping mechanism disposed in the luer portion and configured to limit an extent of a fluid line disposed in the connector, and a retaining mechanism disposed in the tubing portion and configured to retain the fluid line in the connector.

9 Claims, 10 Drawing Sheets

LUER HAVING TUBING RETENTION POCKET BOND

BACKGROUND

Field

Embodiments disclosed are related to medical connectors, and more particularly, to a medical connector having a retaining mechanism for preventing a fluid line coupled thereto from dislodging or separating from the connector due to the reduction of fluid in the fluid line and a stopping mechanism to limit an extent of the fluid line in the connector.

Description of Related Art

Medical connectors are widely used in fluid delivery systems such as those used in connection with intravenous (IV) fluid lines, blood access, hemodialysis, peritoneal dialysis, enteral feeding, drug vial access, etc. Medical connectors may generally connect two fluid lines or tubing Typically, the medical connector may be a hollow tubular structure that receives a fluid line or tubing at one end thereof. The connector provides a flow path for fluid entering from the tubing to exit the connector from the opposite end thereof. The presence of fluid in the tubing may create a hermetic seal between outer surface of the tubing and the inner surface of the medical connector. The seal may prevent the tubing from separating from the medical connector. However, when the fluid is absent in the tubing or when the amount of fluid in the tubing is reduced, the seal may be weakened and the tubing may be separated easily from the connector, thereby creating a "free flow" leak.

SUMMARY

In accordance with at least some embodiments disclosed herein is the realization that the medical connector can fail to function as intended when fluid is absent in the tubing or when the amount of fluid in the tubing is reduced. For example, decrease in the amount of fluid may cause the hermetic seal between outer surface of the tubing and the inner surface of the medical connector to weaken and the tubing may separate easily from the medical connector.

An aspect of the present disclosure provides a connector including a body having a tubing portion and a luer portion axially opposite the tubing portion and connected thereto; an internal passageway defined by an inner circumferential surface of the connector, the passageway extending axially between the tubing portion and the luer portion and in fluid communication therewith; a stopping mechanism disposed in the luer portion and configured to limit an extent of a fluid line disposed in the connector; and a retaining mechanism disposed in the tubing portion, axially offset from the stopping mechanism, and configured to retain the fluid line in the connector.

Another aspect of the present disclosure provides an assembly including a connector having a body having a tubing portion and a luer portion axially opposite the tubing portion and connected thereto, an internal passageway defined by an inner circumferential surface of the connector, the passageway extending axially between the tubing portion and the luer portion and in fluid communication therewith, a stopping mechanism disposed in the luer portion and configured to limit an extent of a fluid line disposed in the connector, and a retaining mechanism disposed in the tubing portion and configured to retain the fluid line in the connector. The assembly may also include a first core pin including a first core pin body having a first base portion and a luer-shaping portion connected to each other, wherein two ledge-forming profiles are defined at a distal end of the first core pin and disposed diametrically opposite each other. The assembly may further include a second core pin including a second core pin body having a second base portion and a tubing-shaping portion connected to each other, wherein a barb-forming profile is defined at a distal end of the second core pin.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Embodiments disclosed are directed to a connector having a retaining mechanism for preventing a fluid line coupled thereto from dislodging and/or separating from the connector in the absence (or reduction) of fluid in the fluid line and a stopping mechanism to limit an extent of the fluid line in the connector. As disclosed herein, the retaining mechanism may include barbed fittings, barbed edges, or similar structures that may retain the fluid line. The retaining mechanism ensures that a seal is maintained between the fluid line and the inner surface of the connector during low pressure conditions (e.g., during the absence of fluid in the fluid line) since there is an interference fit between the fluid line and the connector. As a result, a relatively stronger tensile force is required to be exerted on the fluid line to separate or dislodge the fluid line from the connector. Thus, accidental separation of the fluid line is minimized.

The stopping mechanism may include one or more ledges on an internal surface of the connector that limits the extent of the fluid line in the connector when inserted therein. As discussed below, the connector at the end opposite the end receiving the fluid line includes a female luer fitting. The stopping mechanism prevents the fluid line from extending into the female luer fitting during assembly and thereby ensures correct operation of the medical connector.

Another advantage of the medical connector, according to embodiments disclosed, is that there is not a substantial increase in the manufacturing costs of the medical connector. Existing manufacturing equipment may be modified at minimal costs to manufacture the example medical connector. For example, the core pins of the injection molding equipment used to manufacture the medical connector may be redesigned to create the stopping and retaining mechanisms.

As used herein, the term "fluid line" and any variation thereof refers to medical lines or tubes used to deliver liquids, solvents, or fluids (including gas) to or from a patient under medical care. For example, fluid lines may be used for intravenous (IV) delivery of fluids, fluid drainage, oxygen delivery, a combination thereof, and the like.

As used herein, the terms "medical connector," "connector," and any variation thereof refer to any device used to provide a fluid flow path between two or more fluid lines coupled thereto. For example, the medical connector may be or include a bond pocket or other types of connectors.

Figure 1:
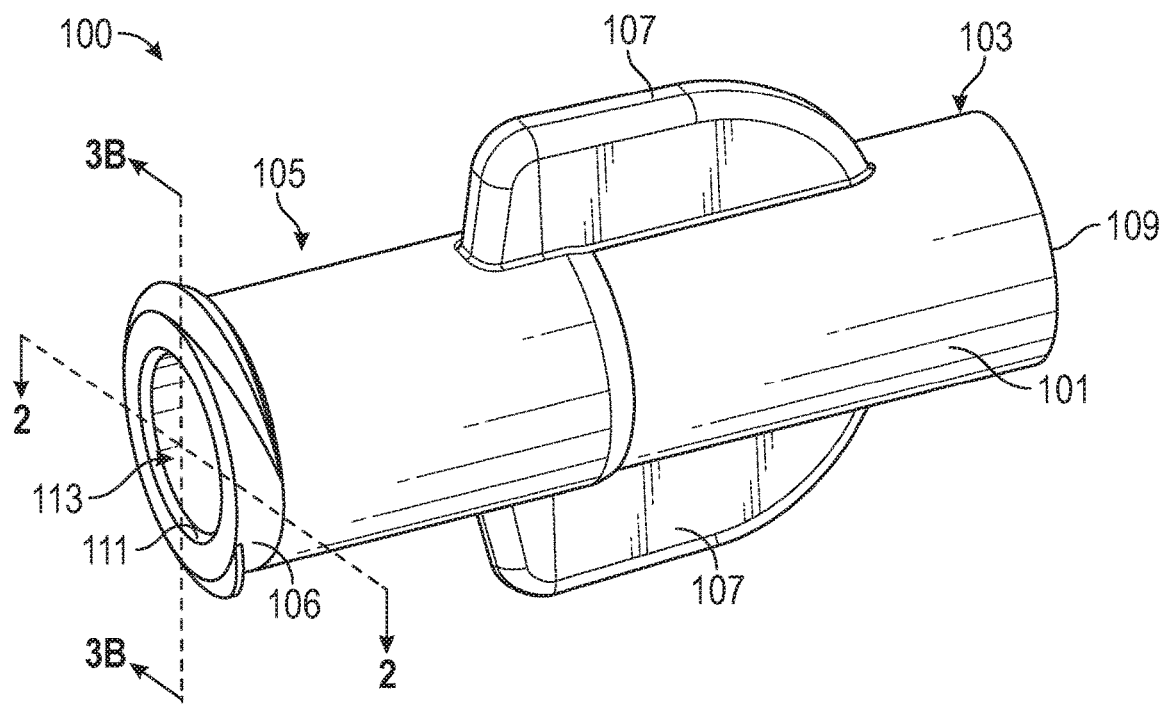
FIG. 1 is a perspective view of a medical connector that may employ the principles of the present disclosure, according to embodiments disclosed

FIG. 1 illustrates an isometric view of a medical connector 100 that may employ the principles of the present disclosure, according to embodiments disclosed. As illustrated, the medical connector (or simply, connector) may include a generally cylindrical body 101 having a "first" or tubing portion 103 and a "second" or luer portion 105 axially opposite the tubing portion 103 and connected thereto. The body 101 also includes two grips 107 disposed on the outer surface of the body 101. Although two grips 107 are illustrated, the number of grips may be increased or decreased as desired. The tubing portion 103 includes a tubing port 109 that is sized and shaped or otherwise configured to receive a fluid line, as discussed below. The luer portion 105 includes a luer port 111 that is sized and shaped or otherwise configured to receive a male luer connector. A flange 106 may be disposed at or adjacent the luer port 111. Another flange (not illustrated) may also be disposed at or adjacent the tubing port 109. The body 101 defines an internal longitudinal passageway or channel 113 extending from the tubing port 109 to the luer port 111 and fluidly connecting the tubing port 109 and the luer port 111 with each other.

Figure 2:
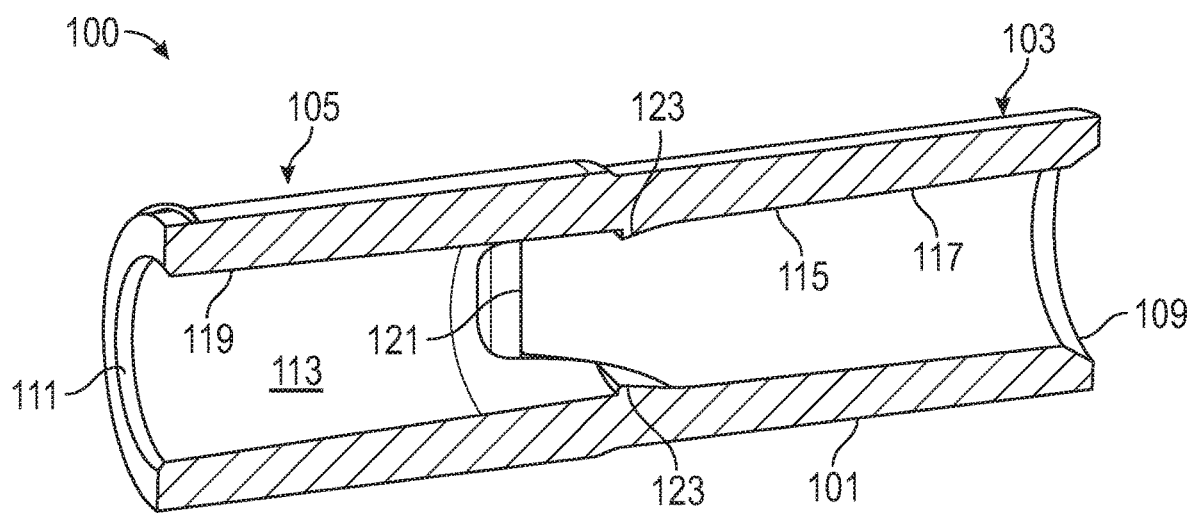
FIG. 2 is a cross-sectional view of the connector of FIG. 1, according to embodiments disclosed.

FIG. 2 is a cross-sectional view of the connector 100, according to embodiments disclosed. As illustrated, the passageway 113 is defined by the inner circumferential surface 115 of the body 101 and is continuous from the tubing port 109 to the luer port 111. The inner circumferential surface 115 in the tubing portion 103 and the luer portion 105 has two non-similar profiles. Specifically, the inner circumferential surface 115 in the tubing portion 103 has a tubing profile 117 and the inner circumferential surface 115 in the luer portion 105 has a luer profile 119 (or luer taper). The tubing profile 117, and thereby the tubing portion 103 of the connector 100, is sized and shaped (or otherwise configured) to receive a fluid line. The luer profile 119, and thereby the luer portion 105 of the connector 100, is sized and shaped (or otherwise configured) to receive standard male luer fittings. The luer profile 119, and thereby the luer portion 105, is ISO-594 compliant.

During assembly, in order to limit the extent of the fluid line inserted, advanced, or otherwise "slipped" into the connector 100, the inner circumferential surface 115 may define include a stopping mechanism. In an example, and as illustrated, the stopping mechanism may be or include one or more, and preferably two ledges 121 (one shown in FIG. 2), protruding (or otherwise projecting) radially inward from the inner circumferential surface 115 and circumferentially separated from each other. In some embodiments with multiple ledges 121, the ledges may be positioned diametrically opposite each other (180° apart) in the passageway 113. In embodiments where there are more than two ledges 121, the ledges may be distributed equally circumferentially around the inner surface 115. In these embodiments, equal distribution can provide equally distributed forces about a tube inserted inside the connector. In some embodiments, the ledges 121 can be distributed asymmetrically about the inner surface 115. The ledges 121 may not be restricted to any particular shape or size as long as the ledges 121 prevent the extent of the fluid line inserted into the connector 100. In an example, a maximum distance by which the ledges 121 project into the passageway 113 is less than or equal to the thickness of the fluid line 151. This prevents the ledges 121 from occluding the fluid travelling the fluid line inserted into the connector 100.

In addition, the inner circumferential surface 115 may also include a retaining mechanism for improving the ability of the connector 100 to retain the fluid line inserted therein and thereby prevent the fluid line from separating (or otherwise dislodging) from the connector 100 during a low pressure condition in the fluid line created due to a reduction in the fluid in the fluid line. In an example, and as illustrated, the retaining mechanism may be or include two barbed features (or barbed fittings) 123 disposed diametrically opposite each other on the inner circumferential surface 115 and in the tubing portion 103. In an example, and as illustrated, the barbed features 123 may be disposed at or adjacent the boundary between the tubing portion and the luer portion 105. Each barbed feature 123 may project radially inward a certain distance from the inner circumferential surface 115 into the passageway 113. In an example, the barbed features 123 may be spike like structures that extend from the inner circumferential surface 115. However, in other embodiments, the barbed features 123 may be ridges or other similar structure that increases friction between the fluid line and inner circumferential surface 115 such that the fluid line may not be easily dislodged from the connector 100, without departing from the scope of the disclosure. In some embodiments, the barbed features 123 may be structured as ramps that have a slight undercut that is configured to slightly compress the fluid line as it is inserted or advanced into the connector, and when the fluid line is pulled to be withdrawn from the connector, the top of the ramp, and in some embodiments the undercut portion, will secure the fluid line within the connector. In some embodiments, the top of the ramp, or the undercut portion, will dig into the tubing when it is attempted to be withdrawn from within the connector, as explained further below.

Figure 3A:
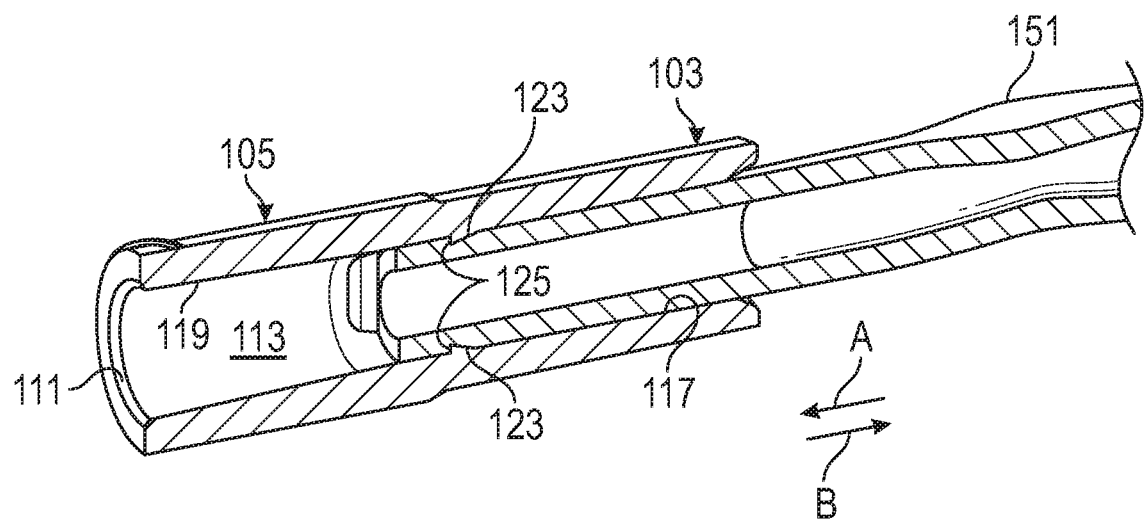
FIG. 3A is a cross-sectional view of the connector of FIG. 2 including a fluid line inserted therein.
Figure 3B:
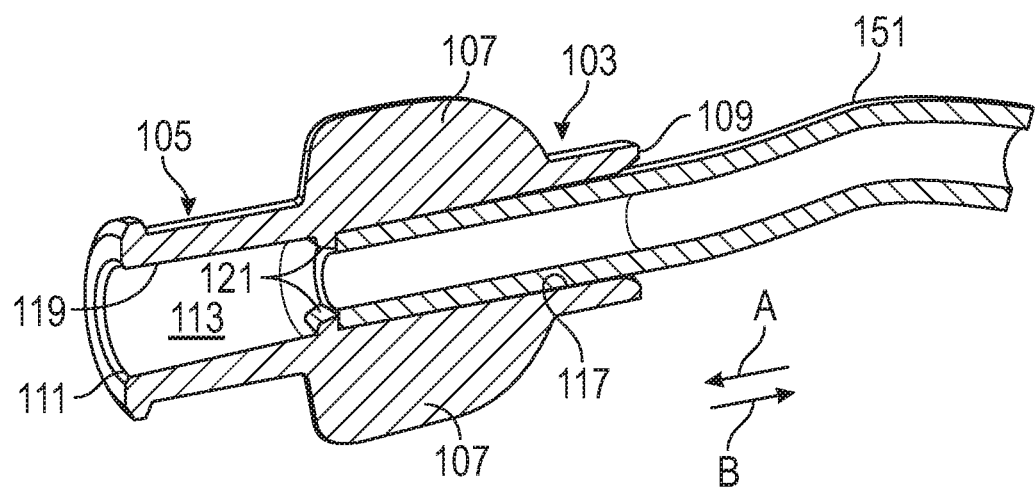
FIG. 3B is a cross-sectional view of the connector of FIG. 1 including a fluid line inserted therein.

FIG. 3A is a cross-sectional view of the connector 100 in FIG. 2 including a fluid line 151 inserted therein. FIG. 3B is a cross-sectional view of the connector 100 in FIG. 1 including the fluid line 151 inserted therein. Referring to FIGS. 3A and 3B, with continued reference to FIGS. 1 and 2, the fluid line 151 may be inserted into the connector 100 generally in the direction of arrow A and each barbed feature 123 may have a tapered distal end 125 that is generally oriented in the direction in which the fluid line 151 is inserted into the connector 100. The fluid line 151 may be inserted into the connector 100 with relative ease. However, the barbed structures 123 may increase the friction between the connector 100 and the fluid line 151 when a tensile force (direction indicated by the arrow B) is applied on the fluid line 151 to remove it from the connector 100. As a result, the tensile force required to remove or otherwise dislodge the fluid line 151 from the connector 100 is increased and thus the fluid line 151 is better secured in the connector 100. Further, the fluid in the fluid line 151 may exert pressure in a radially outward direction, which may further increase the friction between the fluid line 151 and the barbed feature 123.

When the fluid line 151 is inserted into the connector 100, the fluid line 151 contacts the ledges 121 after passing over the barbed features 123. As a result, the extent of the fluid line 151 in the connector 100 is limited and the fluid line 151 is prevented from entering the luer portion 105. In some embodiments, the ledges 121 and the barbed features 123 are slightly separately, such that the fluid line 151 passes over the barbed features 123, and further advancement will cause them to contact the ledges 121. The tubing portion 103 including the tubing profile 117 may thus extend between the ledges 121 and the tubing port 109, and the luer portion 105 including the luer profile 119 may extend between the luer port 111 and the ledges 121.

It should be noted that the locations of the ledges 121 and the barbed features 123 on the inner circumferential surface 115 in FIGS. 3A and 3B are merely examples, and the locations may be changed, without departing from the scope of the disclosure. Further, although FIGS. 2, 3A, and 3B illustrate two ledges 121 and two barbed features 123, the number of ledges and barbed features are not limited thereto and may be increased or decreased, without departing from the scope of the disclosure. In an example, multiple ledges 121 may be disposed at regular intervals along the inner circumferential surface 115. However, in other embodiments, the ledges 121 may be disposed at irregular intervals along the inner circumferential surface 115. Similarly, multiple barbed features 123 may be disposed at regular intervals along the inner circumferential surface 115. However, in other embodiments, the barbed features 123 may be disposed at irregular intervals. The circumferential extent of barbed features 123 may be around a quarter of a quadrant of the inner circumferential surface. However, in other examples, the circumferential extent of the barbed features 123 may be increased or decreased as required by application or design, and without departing from the scope of the disclosure.

Figure 4A:
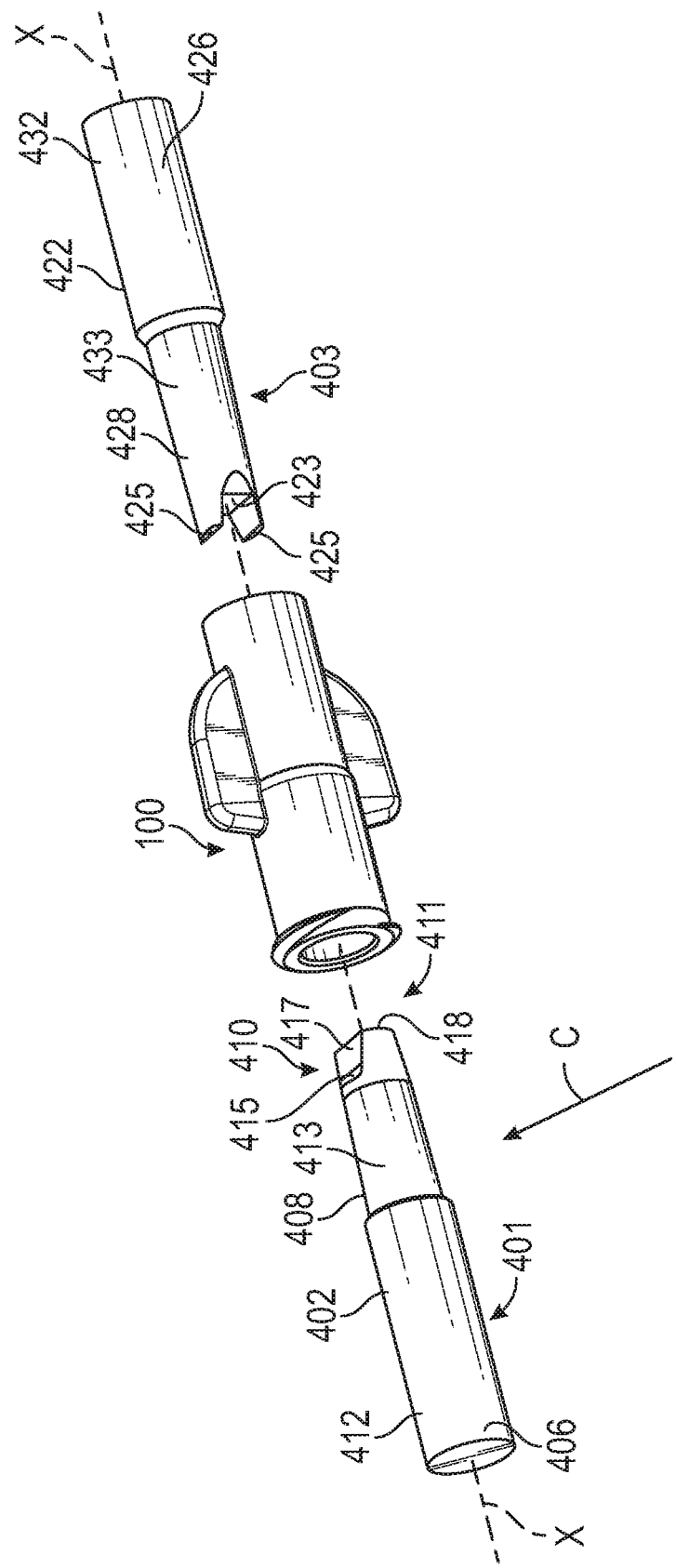
FIG. 4A illustrates the connector of FIG. 1 and core pins used to form the tubing profile and the luer profile on the inner circumferential surface of the connector.

In an example, the connector 100 may be manufactured using an injection molding process. However, other manufacturing processes may also be used to manufacture the connector 100, without departing from the scope of the disclosure. FIG. 4A illustrates the connector 100 and core pins 401 and 403 used to form the tubing profile 117 and the luer profile 119 of the inner circumferential surface 115. In an example, the core pin 401 may form the luer profile 119 of the inner circumferential surface 115 and the core pin 403 may form the tubing profile 117 of the inner circumferential surface 115. For the sake of brevity, the processing steps and molds used for creating the features (e.g., grips 107) on the outer surface of the body 101 are omitted.

Referring to FIG. 4A, core pin 401 has a generally elongated body 402 having a base portion 406 and a luer-shaping portion 408. The base portion 406 has a generally cylindrical outer surface 412 having a diameter larger than the largest diameter of the luer-shaping portion 408. The luer-shaping portion 408 has an outer surface 413 that is shaped to form the luer profile 119 (FIG. 2). One or more ledge-forming profiles 410 may be formed on the outer surface 413 proximate a distal end 411 of the luer-shaping portion 408. In FIG. 4A, the core pin 401 has two ledge-forming profiles 410 (one hidden from view) formed diametrically opposite each other at the distal end 411.

Figure 4B:
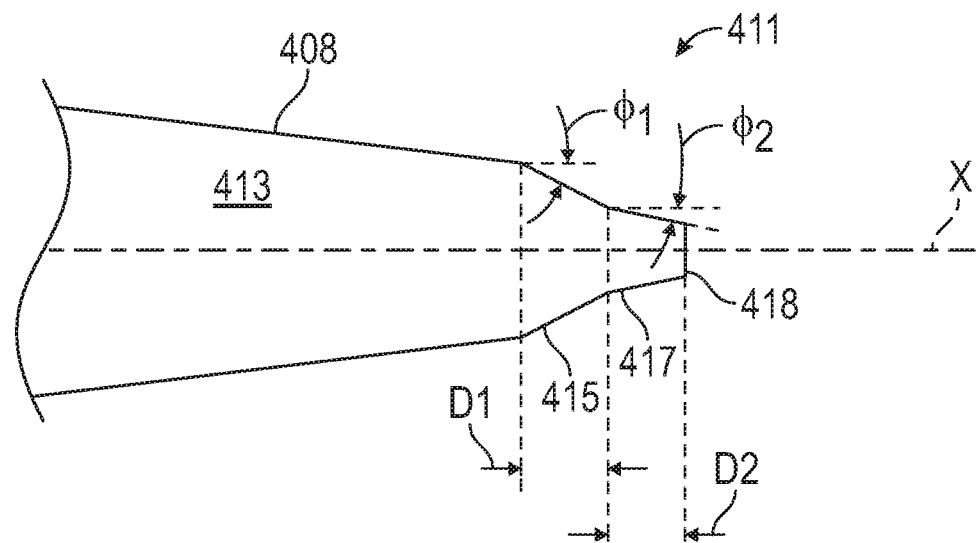
FIG. 4B illustrates the distal end of the core pin of FIG. 4A viewed in the direction of arrow C and including two ledge-forming profiles.

Referring briefly to FIG. 4B, illustrated is a front (or elevation) view of the core pin 401 and showing the two ledge-forming profiles 410 in greater detail, according to embodiments disclosed. As illustrated, the ledge-forming profiles 410 are formed (or otherwise defined) in the outer surface 413 proximate the distal end 411 of the core pin 401. Although FIG. 4B illustrates the core pin 401 having two ledge-forming profiles 410 formed diametrically opposite each other at the distal end 411, in other examples, the number and placement of ledge-shaping profiles may increase or decrease depending on the number of ledges and barbed features to be formed in the connector 100, without departing from the scope of the disclosure.

Each ledge-forming profile 410 includes a first planar surface 415 and a second planar surface 417, each formed (or otherwise defined) in the outer surface 413. The first planar surface 415 extends axially a distance D1 at a first angle $\varphi 1$ with respect to the axis X of the assembly comprising the connector 100 and core pins 401 and 403. The second planar surface 417 extends axially a distance D2 at a second angle $\varphi 2$ with respect to the axis X and from the first planar surface 415 to the distal end 411. It should be noted that, when assembled, the individual axes of the core pins 401 and 403 and the connector 100, and the axis X are coincident. In an example and as illustrated, the first angle $\varphi 1$ is greater than the second angle $\varphi 2$. As discussed further below, the shapes and sizes of the ledges 121 of the connector 100 may be based (at least partly) on the first angle $\varphi 1$ and the first planer surface 415. The distal end 411 may include a transverse end surface 418 disposed perpendicular to the axis X and connected to the second planar surface 417.

Returning to FIG. 4A, the core pin 403 also has a generally elongated body 422 having base portion 426 having a cylindrical outer surface 432 and tubing-shaping portion 428 having a cylindrical outer surface 433. The diameter of the base portion 426 is greater than the diameter of the tubing-shaping portion 428. The cylindrical outer surface 433 is shaped and sized to form the tubing profile 117 (FIG. 2) of the tubing portion 103.

Figure 4C:
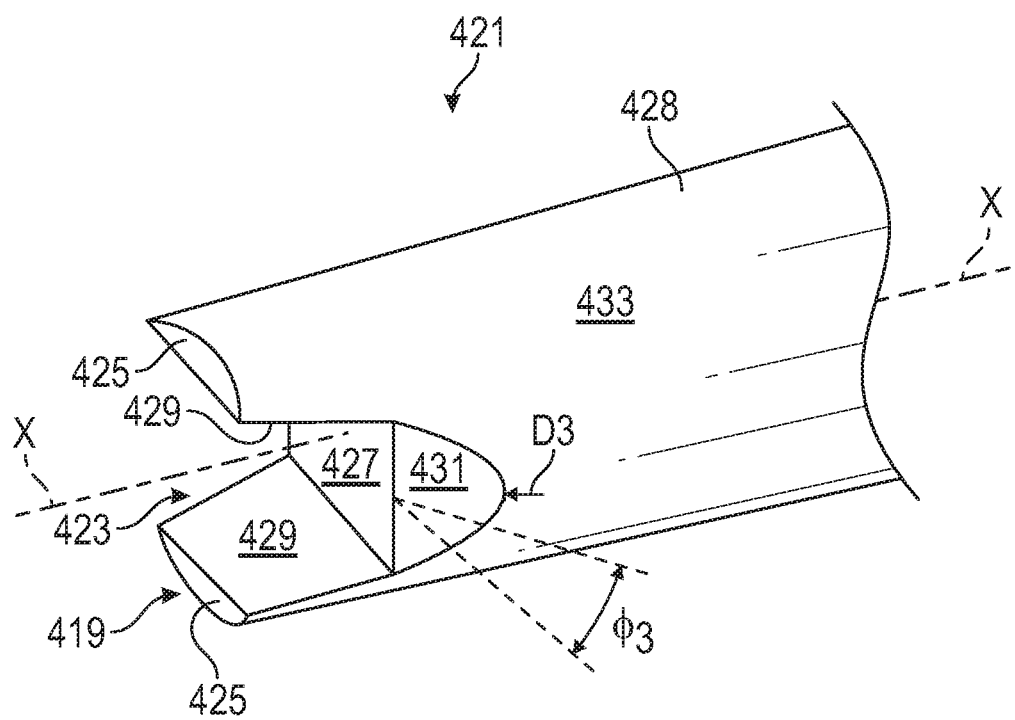
FIG. 4C is a perspective view of the distal end of the tubing-shaping portion of the core pin of FIG. 4A.

FIG. 4C illustrates the distal end 421 of the tubing-shaping portion 428 of the core pin 403 in more detail. As illustrated, at the distal end 421, the tubing-shaping portion 428 may include barb-forming profile 419 including two axially extending prongs 425 and a cavity (or a generally concave cutout) 423 defined between the two prongs 425. The cavity 423 may be defined by a planar bottom surface 427 disposed perpendicular to the axis X and angled inner surfaces 429 of the prongs 425. As illustrated, the inner surfaces 429 are angled with respect to the axis X. Two chamfered edges 431 (one hidden from view) may be defined between the planar bottom surface 427 and the cylindrical outer surface 432 and may be disposed at diametrically opposite ends of the tubing-shaping portion 428. Each chamfered edge 431 may extend axially a distance D3 between the planar bottom surface 427 and the cylindrical outer surface 433. An angle φ3 may be defined between each chamfered edge 431 and the planar bottom surface 427. The angle φ3 and the distance D3 may at least partially determine the radial extent of the barbed features 123 into the passageway 113 of the connector 100.

Figure 5A:
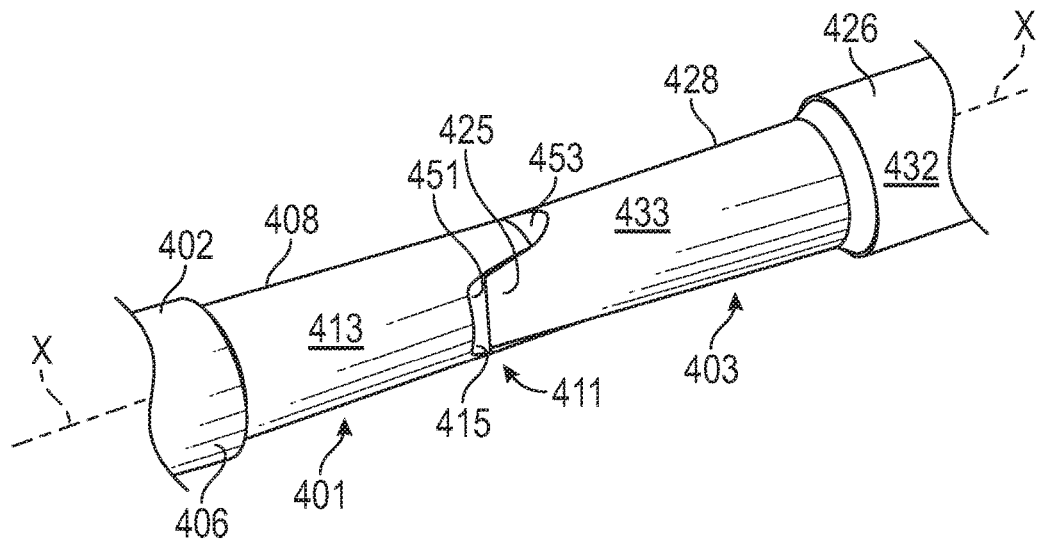
FIG. 5A illustrates the core pins of FIG. 4A contacting each other at respective the distal ends.

FIG. 5A illustrates the core pins 401 and 403 contacting each other at the respective distal ends 411 and 421. For the sake of illustration, the core pins 401 and 403 are illustrated rotated 90° from their positions in FIG. 4A and the connector 100 is omitted from FIG. 5A. In an example, the connector 100 (FIGS. 1-3B) may be manufactured using an injection molding process. The connector 100 may be made of plastic or similar material that can be molded into a desired shape. An external mold (not illustrated) may be used to create the external features of the connector 100. These external features may include the grips 107, the flange 106, and the outer surface of the cylindrical body 101. The passageway 113, tubing profile 117, the luer profile 119, the ledges 121, and the barbed features 123 may be formed using the core pins 401 and 403.

During manufacture, material forming the connector 100 may be placed in a molding tool including the core pins 401 and 403 axially aligned with each other. The core pins 401 and 403 may be brought together from axially opposite ends into the material. The material may be in a semi-solid, malleable state in order to mold it into a desired shape. The core pins 401 and 403 may be brought towards each other until the core pins 401 and 403 shut against each other, as illustrated in FIG. 5A.

When the core pins 401 and 403 shut against each other, the distal end 411 of the core pin 401 is received into the distal end 421 of the core pin 403. More specifically, the distal end 411 including the ledge-forming profiles 410 is received into the cavity 423 of the barb-forming profile 419 such that the transverse end surface 418 contacts (or shuts against) the planar bottom surface 427 and the angled inner surfaces 429 of the prongs 425 contact the second planar surfaces 417. The ledge-forming profiles 410 and the barb-forming profile 419 cooperatively form the stopping mechanism and the retaining mechanism. Specifically, when the core pins 401 and 403 shut against each other, two cavities 451 (one shown) are formed (or otherwise defined) by the first planar surfaces 415 and prongs 425, and two cavities 453 (one shown) are formed by the luer-shaping portions 408 and the chamfered edges 431. The material of the connector 100 in the cavity 451 forms the ledges 121 and the material in the cavity 453 forms the barbed features 123.

Figure 5B:
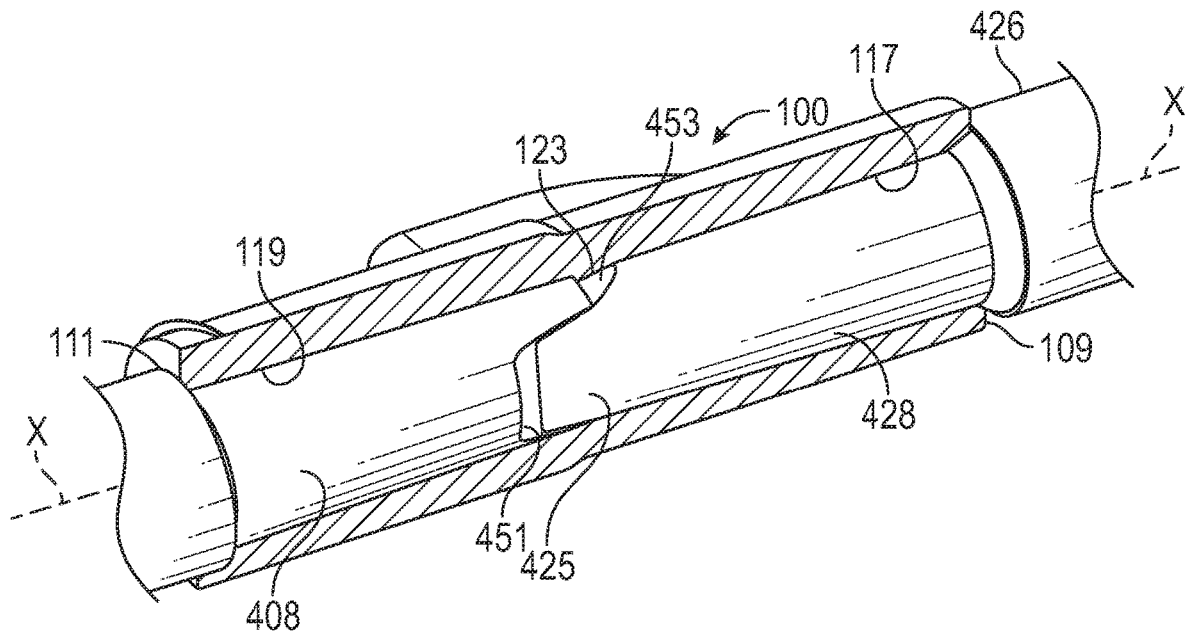
FIG. 5B is a cutaway view of the connector of FIG. 2 including the core pins of FIG. 4A disposed therein.

FIG. 5B is a cutaway drawing of the connector 100 including the core pins 401 and 403 contacting each other. As illustrated, when the core pins 401 and 403 shut against each other, the base portion 406 may contact the opening of the luer port 111 and the base portion 426 may contact the opening of the tubing port 109. According to the disclosed embodiments, the ledges 121 may be similar to each other, for instance, in shape and size. Likewise, the barbed features 123 may be similar to each other, for instance, in shape and size. However, in other embodiments, the ledges 121 may be dissimilar to each and the barbed features 123 may be dissimilar to each other.

Figure 5C:
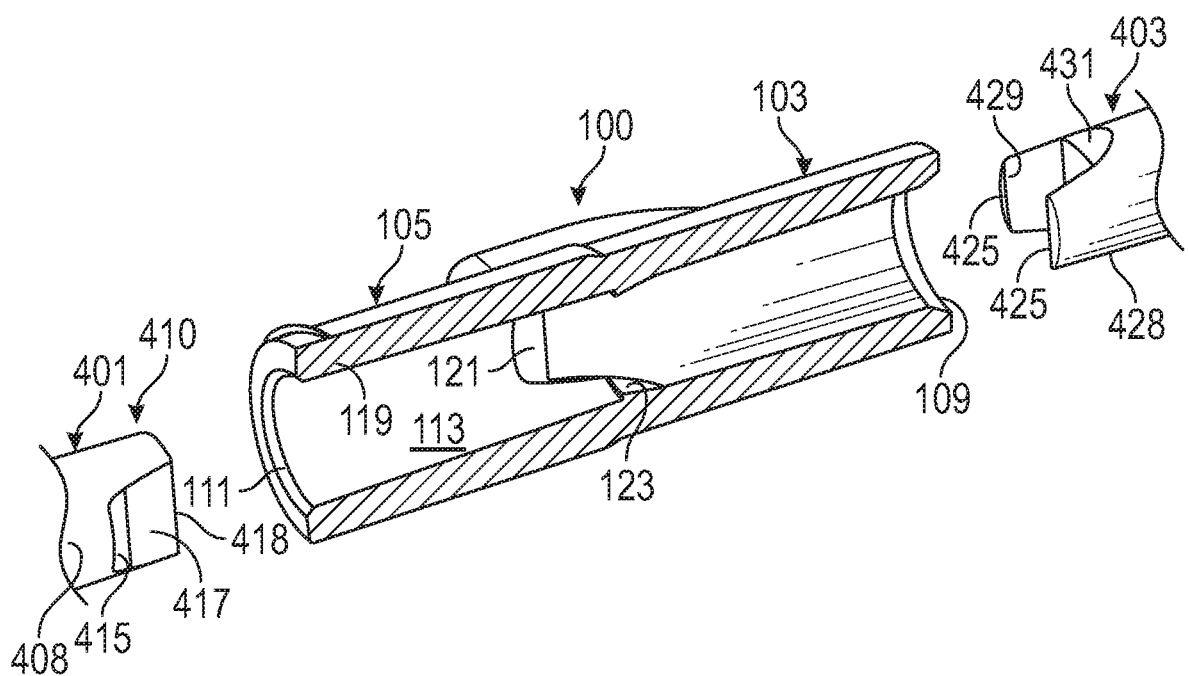
FIG. 5C is a cutaway view of the connector of FIG. 2 with the core pins disposed outside the connector.

FIG. 5C illustrates a cutaway drawing of the connector 100 and the core pins 401 and 403 separated from each other. FIG. 5C is similar FIG. 5B, except that the core pins 401 and 403 are illustrated outside the connector 100. For the sake of illustration, the portion of the inner circumferential surface 115 including the tubing profile 117 and the portion of the inner circumferential surface 115 including the luer profile 119 are depicted for the core pins 401, 403 that form the tubing profile 117 and luer profile 119.

Figure 5D:
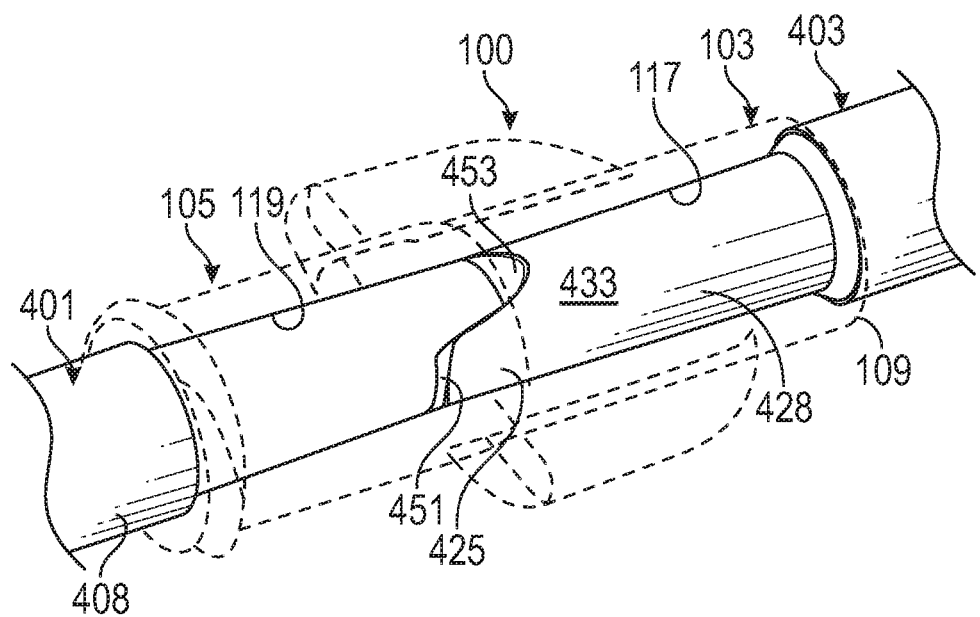
FIG. 5D is a perspective view of the connector (illustrated in phantom) of FIG. 1 including the core pins of FIG. 4A contacting each other therein.

FIG. 5D is a perspective view of the connector (illustrated in phantom) of FIG. 1 including the core pins of FIG. 4A contacting each other therein.

According to the embodiments disclosed above, the connector 100 includes two diametrically opposite ledges 121 and two diametrically opposite barbed features 123 formed therein. The ledges 121 and the barbed features 123 do not overlap each other in the radial direction.

In other embodiments, the connector 100 may include a single ledge and a single barbed feature extending along the inner circumferential surface 115. In such a case, the single ledge may extend between about 180° to about 270° along the inner circumferential surface 115 and the single barbed feature may extend the remaining portion of the inner circumferential surface 115. Alternatively, the single barbed feature may extend about 180° to 270° along the inner circumferential surface 115 and the single ledge may extend the remaining portion of the inner circumferential surface 115. In each instance, the single ledge and the single barbed feature may also not overlap each other in the radial direction.

In still other embodiments, the connector may include a single ledge and multiple barbed features. In an alternative embodiment, the connector may include multiple ledges and a single barbed feature. In both instance, the ledge(s) and the barbed feature(s) may not radially overlap each other.

For correct operation of the connector 100, both at least one ledge 121 and at least one barbed feature 123 are required. If, for instance, the connector 100 excluded the barbed features 123, then, while the extent of a tubing in the connector 100 may be limited, the tubing may be easily dislodge or separate from the connector 100. Similarly, if the connector 100 excluded the ledges 121, then, while the tubing may be retained in the connector 100 under low fluid pressure conditions, the extent of the tubing in the connector 100 may not be limited and the tubing may enter the luer portion 105 of the connector 100 and block against a male luer fitting positioned in the luer portion 105.

In each of the embodiments discussed above, the ledges 121 and the barbed features 123 are axially offset or separated from each other. The offset or the separation between the ledges 121 and the barbed features 123 is not limited to any particular distance. An advantage of this arrangement is that, when the tubing passes over the barbed features 123, there is a less likely chance that the tubing will extend past the ledges 121. This is because, the barbed features 123 "pinch" the tubing and, as the tubing passes over the barbed features 123, the tubing protrudes radially outwardly towards the inner circumferential surface 115 and increase the probability of the tubing contacting the ledges 121.

In an example, the barbed features 123 may have a greater circumferential extent (or circumferential width) than the ledges 121. However, in other embodiments, the barbed features 123 and the ledges 121 may have the same circumferential extent.

Figure 6A:
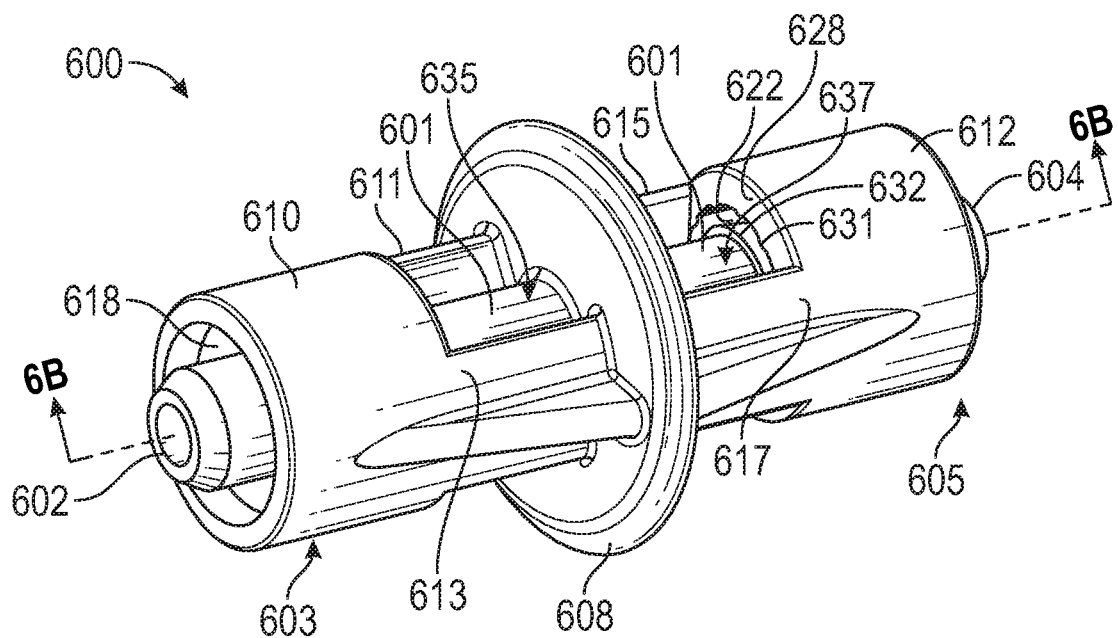
FIG. 6A is a perspective view of a medical connector that may employ the principles of the present disclosure, according to embodiments disclosed.
Figure 6B:
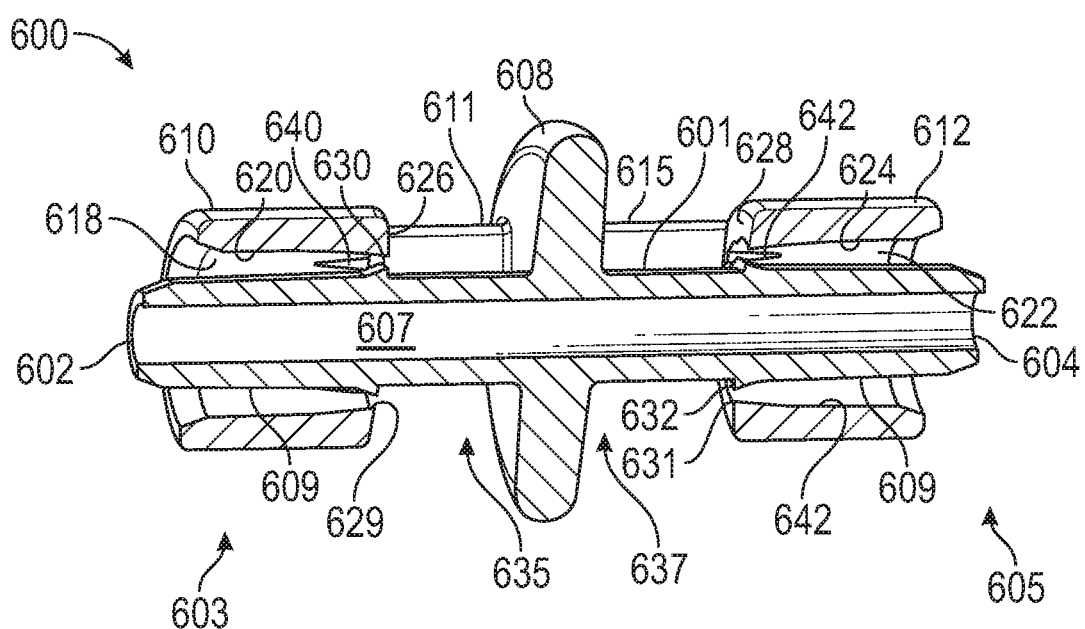
FIG. 6B illustrates a cross-sectional view of the medical connector of FIG. 6A.

FIG. 6A is a perspective view of a medical connector 600 that may employ the principles of the present disclosure, according to embodiments disclosed. FIG. 6B illustrates a cross-sectional view of the medical connector 600. Referring to FIGS. 6A and 6B, the medical connector 600 may include a tubular structure 601 (or simply, a tubular) having a first port 602 at a first end 603 and a second port 604 at a second end 605 longitudinally opposite the first end 603. The tubular 601 defines an internal longitudinal passageway or channel 607 extending from the first port 602 to the second port 604 and fluidly connecting the first port 602 and the second port 604 with each other. A central collar 608 may be disposed about the tubular 601 and may be connected to the outer circumferential surface 609 of the tubular 601. Although the central collar 608 is illustrated disposed midway along the tubular 601, the central collar 608 may be located at any desired location along the tubular. Further, in other examples, the tubular 601 may include more than one central collar.

A first cylindrical collar 610 may be disposed about the tubular 601 at the first end 603 and may be connected to the central collar 608 via connectors 611 and 613 that extend between central collar 608 and an inner circular end face 626 of the first cylindrical collar 610. The first cylindrical collar 610 may be radially spaced from the tubular 601 such that a radially and axially extending gap 618 may be defined between the inner circumferential surface 620 of the first cylindrical collar 610 and the outer circumferential surface 609 of the tubular 601. Similarly, a second cylindrical collar 612 may be disposed about the tubular 601 at the second end 605 and may be connected to the central collar 608 via connectors 615 and 617 that extend between central collar 608 and an inner circular end face 628 of the second cylindrical collar 612. The second cylindrical collar 612 may be radially spaced from the tubular 601 such that a radially and axially extending gap 622 may be defined between the inner circumferential surface 624 of the second cylindrical collar 612 and the outer circumferential surface 609 of the tubular 601.

A plurality of ribs 640 may be arranged circumferentially spaced from each other on the inner circumferential surface 620 of the first collar 610. The ribs 640 may be tapered and may extend axially a certain distance from the inner circular end face 626 along the inner circumferential surface 620. For instance, the ribs 640 may be wider at the end that contacts the inner circular end face 626 and may taper axially along the inner circumferential surface 620 in the direction of the first port 602. Each rib 640 may define an edge 629 with the inner circular end face 626 that may protrude into the gap 618. The outer circumferential surface 609 may include a first barbed feature 630 adjacent the first end 603 that may protrude radially outward into the gap 618 from the outer circumferential surface 609 and extend circularly on the outer circumferential surface 609. In an embodiment and as illustrated, the first barbed feature 630 may be axially aligned with the edges 629 of the plurality of ribs 640. However, in other embodiments, the first barbed feature 630 may be axially offset from the edges 629.

A plurality of ribs 642 may be arranged circumferentially spaced from each other on the inner circumferential surface 624 of the second collar 612. The ribs 642 may be tapered and may extend axially a certain distance from the inner circular end face 628 along the inner circumferential surface 624. For instance, the ribs 642 may be wider at the end that contacts the inner circular end face 628 and may taper axially along the inner circumferential surface 624 in the direction of the second port 604. Each rib 642 may define an edge 631 with the inner circular end face 628 that may protrude into the gap 622. The outer circumferential surface 609 may include a second barbed feature 632 adjacent the second end 605 that may protrude radially outward into the gap 622 from the outer circumferential surface 609 and extend circularly on the outer circumferential surface 609. In an embodiment and as illustrated, the second barbed feature 632 may be axially aligned with the edges 631 of the plurality of ribs 642. However, in other embodiments, the second barbed feature 632 may be axially offset from the edges 631, without departing from the scope of the disclosure. The ribs 640 and 642 facilitate relatively easy insertion of a fluid line on the tubular 601 and also permit fluid lines of different wall thicknesses to be coupled to the connector 600. In an embodiment, the ribs 640 and 642 may be arranged at regular intervals along the respective inner circumferential surfaces 620 and 624. However, in other embodiments, the ribs 640 and 642 may be arranged at irregular intervals, without departing from the scope of the disclosure.

The first collar 610 may be axially separated from the central collar 608 and an opening 635 may be defined between the first collar 610 and the central collar 608. Likewise, the second collar 612 may be axially separated from the central collar 608 and an opening 637 may be defined between the second collar 612 and the central collar 608. The openings 635 and 637 may be through openings such that the tubular 601 may be visible via the openings 635 and 637.

Figure 6C:
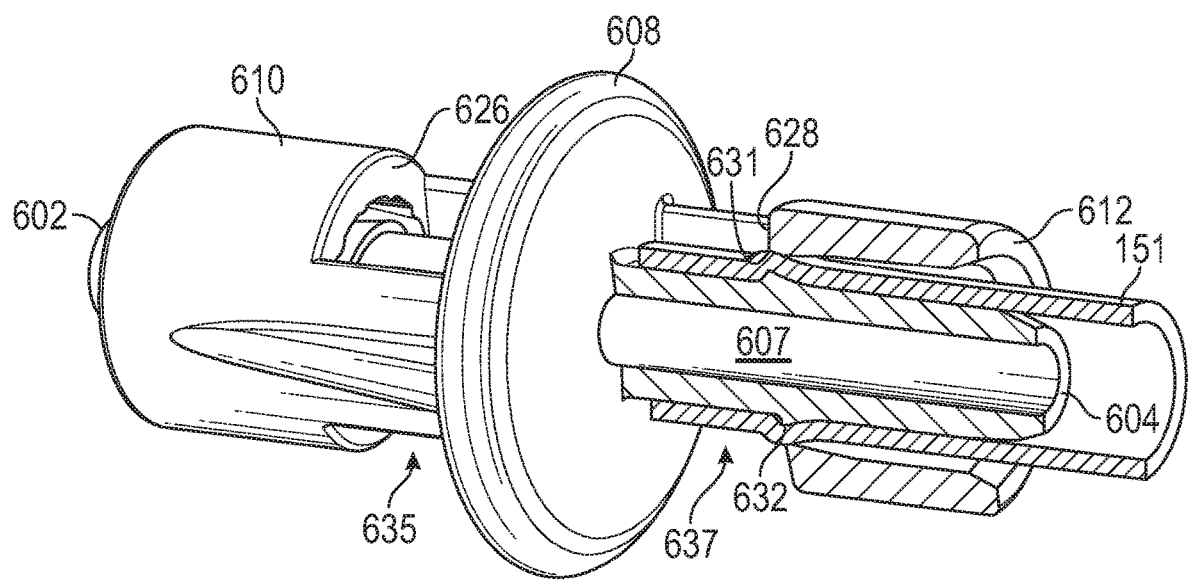
FIG. 6C is a partial cross-sectional view of the connector of FIG. 6A including a fluid line coupled to the second port, according to embodiments disclosed.

FIG. 6C is a partial cross-sectional view of the connector 600 including a fluid line 151 coupled to the second port 604, according to embodiments disclosed. The fluid line 151 may be coupled by sliding (or, "slipping") the fluid line 151 over the tubular 601 in the direction of the central collar 608. When sliding, the fluid line 151 may be pushed over and beyond the barbed feature 632. Hydrostatic pressure due to fluid in the fluid line 151 may cause the fluid line 151 to expand and, as a result, dislodge or slide off from the tubular 601. The barbed feature 632 and the edges 631 may contact the outer surface of the fluid line 151, thereby creating an interference fit between the fluid line 151 and the connector 600. As a result, a relatively stronger tensile force is required to separate or dislodge the fluid line 151 from the connector 600, and the fluid line 151 may not be easily dislodged due to presence of fluid. Thus, accidental separation of the fluid line 151 is minimized. The central collar 608 may prevent further axial movement of the fluid line 151 on the tubular 601. The opening 637 may provide a visual indication of the extent of the fluid line 151 on the tubular 601. A fluid line may be coupled to the first port 602 in a similar manner, and an explanation thereof is omitted for the sake of brevity.

In an embodiment, a solvent may optionally be applied over the tubular 601 to permit relatively easy insertion of the fluid line 151 over the tubular 601. For example, the solvent may be applied over the tubular 601 between the barbed feature 630 and the first port 602, and between the barbed feature 632 and the second port 604. The solvent may be applied by dipping the connector 600 over a custom designed fixture that applied the solvent.

In an embodiment, the fluid line 151 may be coupled to the connector 600 using heat staking. In this case, the solvent may not be used. Heat staking may cause the fluid lien 151 to adhere to the tubular 601 and compress on the tubular 601.

Figure 7A:
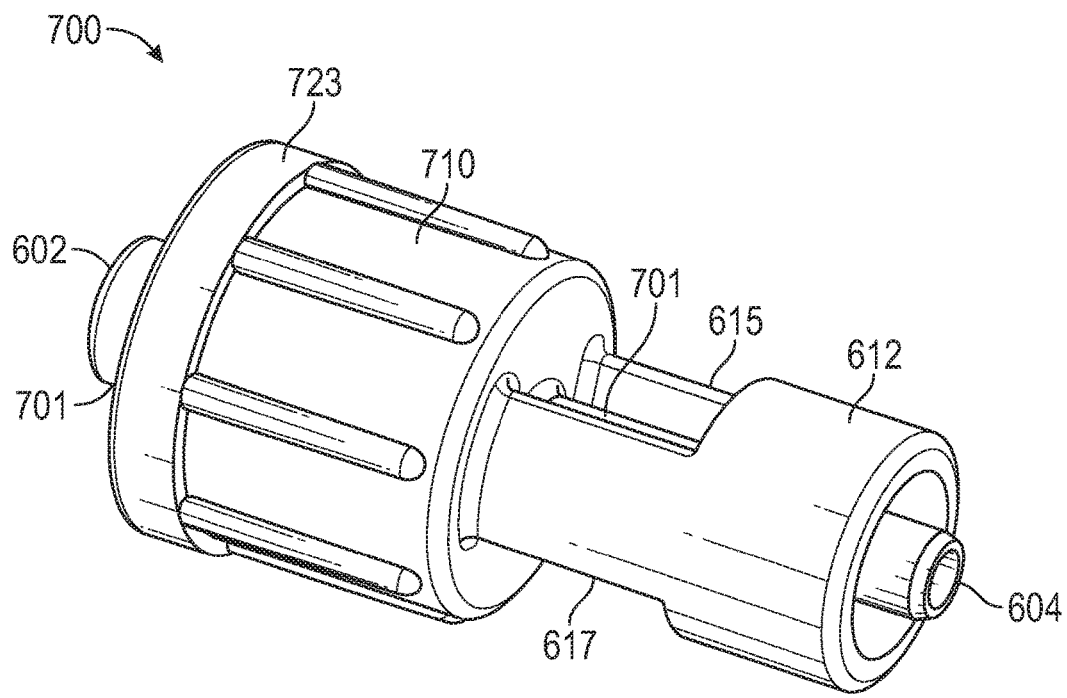
FIG. 7A is a perspective view of a medical connector that may employ the principles of the present disclosure, according to embodiments disclosed.
Figure 7B:
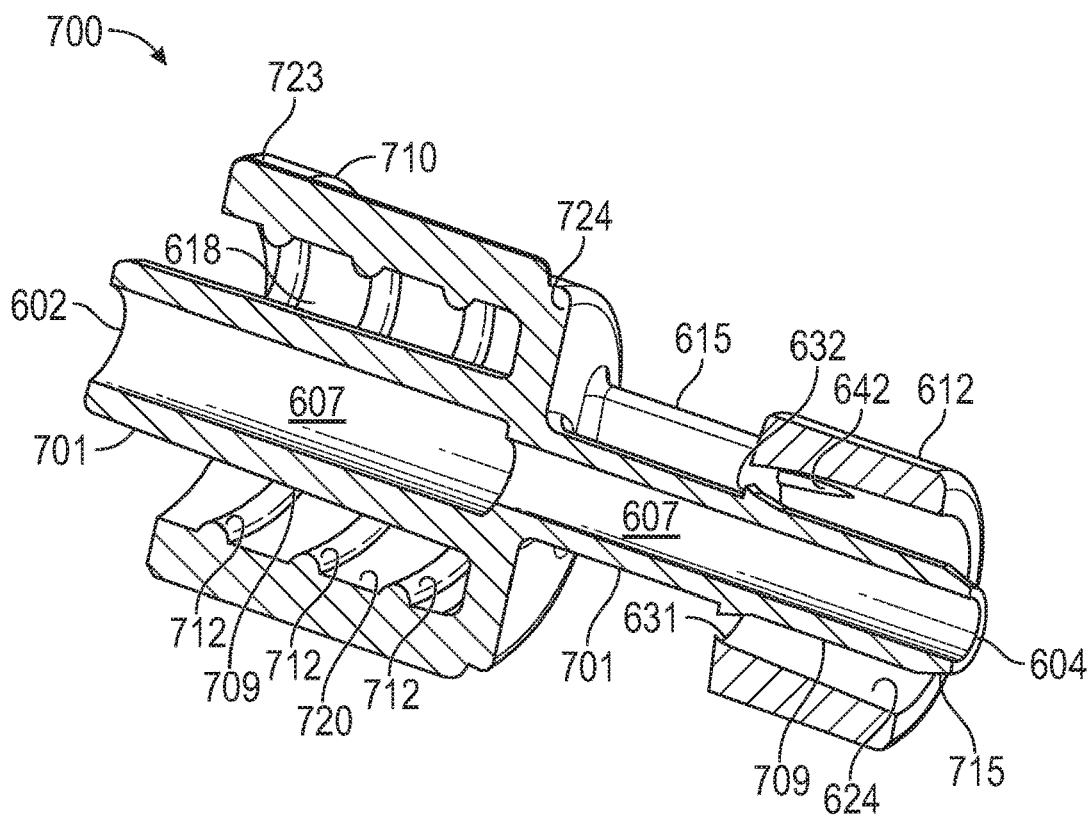
FIG. 7B illustrates a cross-sectional view of the medical connector of FIG. 7A.

FIG. 7A is a perspective view of a medical connector 700 that may employ the principles of the present disclosure, according to embodiments disclosed. FIG. 7B illustrates a cross-sectional view of the medical connector 700. The medical connector 700 may be similar in some respects to the medical connector 600 of FIGS. 6A-6C and, therefore, may be best understood with reference thereto, where like numerals represent like element not described again. As illustrated, the structure of the connector 700 may be similar to the structure of the connector 600 to the right of the central collar 608 in FIGS. 6A and 6B.

In the connector 700, the central collar 608 and the first collar 610 may be omitted and the connector 700 may instead include a third cylindrical collar 710 disposed about a tubular 701 and partially enclosing the tubular 701. The third collar 710 may be coupled to the outer circumferential surface 609 of the tubular 601 via a circular end wall 724. The distal end 723 of the third collar 710 opposite the circular end wall 724 and adjacent first the port 602 may not be connected to the tubular 701. The tubular 701 may include a first portion extending between the first port 602 and the circular end wall 724. The outer circumferential surface 709 of the tubular 701 in the first portion may have a luer profile (ISO-594 compliant).

In an embodiment, and as illustrated, the tubular 701 may extend a certain distance beyond the distal end 723. However, in other embodiments, the port 602 and the distal end 723 may be aligned axially, without departing from the scope of the disclosure.

The inner circumferential surface 720 of the third collar 710 may include a plurality of threads 712 disposed along the inner circumferential surface 720 and protruding radially inward from the inner circumferential surface 720. The threads 712 may engage corresponding threads on a female luer (or other profiles) when coupled thereto.

The tubular 701 may include a second portion extending between the second port 604 and the circular end wall 724. The outer circumferential surface 709 of the tubular 701 may define a lead-in taper profile 715 at the second port 604. The lead-in taper profile 715 may permit fluid line 151 (FIG. 7C) to be inserted since the distal end of the lead-in taper profile 715 has a diameter smaller than the inner diameter of the fluid line 151.

As illustrated, the passageway 607 may extend from the port 602 to the port 604 and fluidly connecting the port 602 and the port 604 with each other. In an embodiment, and as illustrated, the inner diameter of the passageway 607 in the first portion may be greater than the inner diameter of the passageway 607 in the second portion. However, in other embodiments, the inner diameter of the passageway 607 in the first portion may be less than the inner diameter of the passageway 607 in the second portion. In still some embodiments, the inner diameter of the passageway 607 in the first portion may be same as the inner diameter of the passageway 607 in the second portion.

Figure 7C:
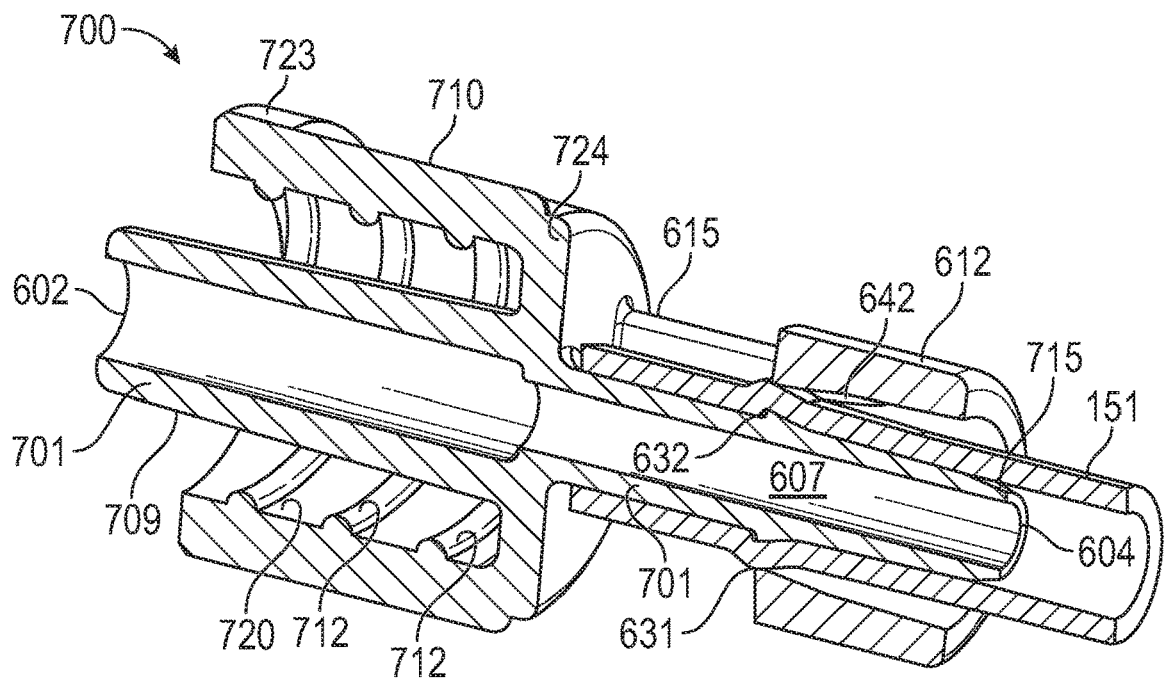
FIG. 7C illustrated a fluid line coupled to the connector of FIG. 7A.
Figure 7D:
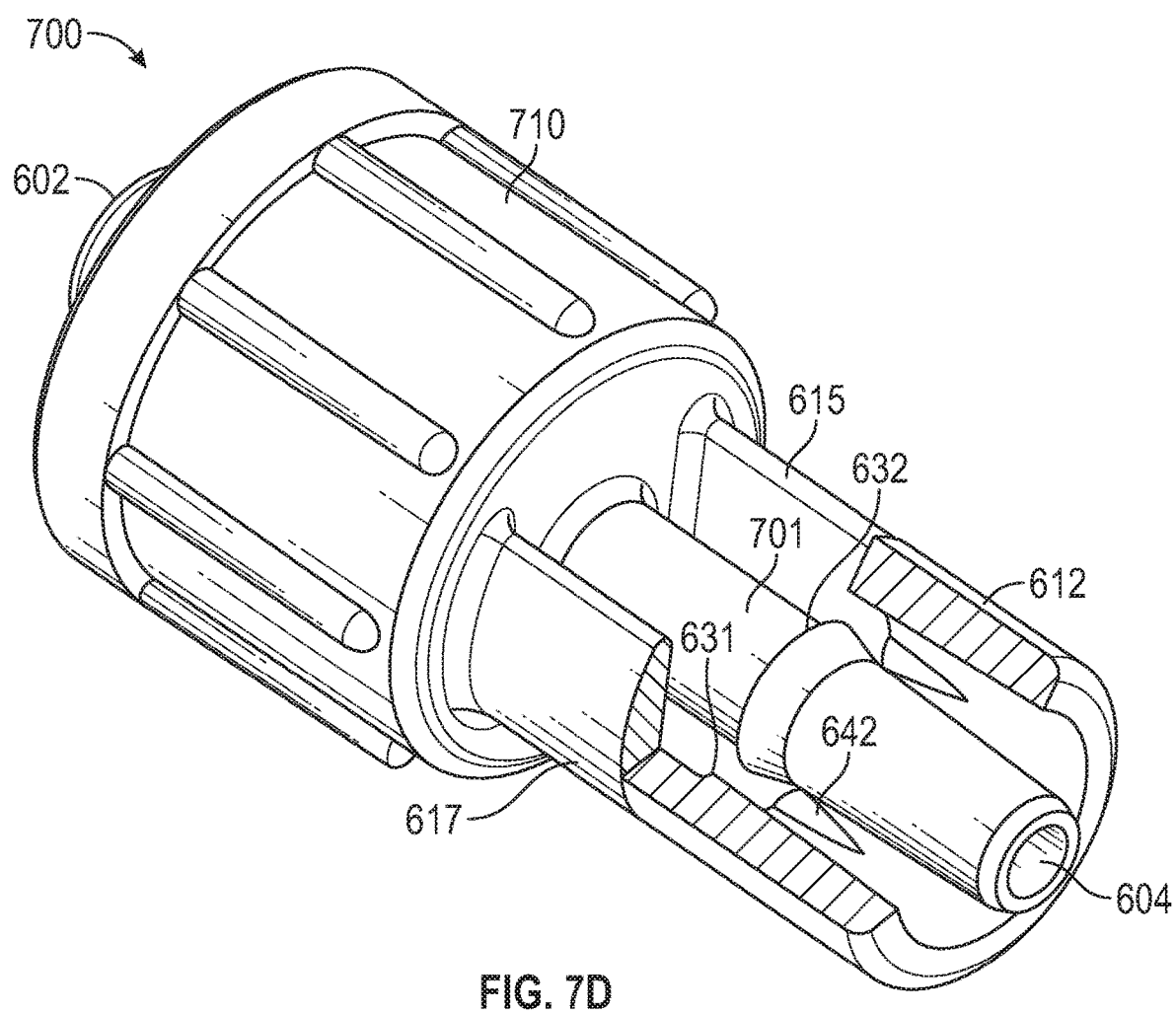
FIG. 7D illustrates a partial cutaway view of the connector of FIG. 7A.

FIG. 7C illustrated a fluid line 151 coupled to the connector 700. As illustrated the tubular 701 is inserted into the fluid line 151 such that the fluid line passes over and beyond the second barbed feature 632 and the edges 631. FIG. 7D illustrates a partial cutaway view of the connector 700.

Referring to FIGS. 6A-6C and 7A-7C, it will be understood by one skilled in the art that tubular 601 at either one or both ends 603 or 605 in FIGS. 6A-6C may have a luer profile.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1: A connector, comprising: a body having a tubing portion and a luer portion axially opposite the tubing portion and connected thereto; an internal passageway defined by an inner circumferential surface of the connector, the passageway extending axially between the tubing portion and the luer portion and in fluid communication therewith; a stopping mechanism disposed in the luer portion and configured to limit an extent of a fluid line disposed in the connector; and a retaining mechanism disposed in the tubing portion, axially offset from the stopping mechanism, and configured to retain the fluid line in the connector.

Clause 2: The connector of clause 1, wherein the inner circumferential surface includes a tubing profile in the tubing portion and a luer profile in the luer portion.

Clause 3: The connector of clause 1, wherein the tubing portion includes a tubing port configured to receive a fluid line and the luer portion includes a luer port configured to receive a male luer connector, the tubing port and the luer port being in fluid communication through the internal passageway.

Clause 4: The connector of clause 1, wherein the stopping mechanism includes one or more ledges projecting radially inward from the inner circumferential surface.

Clause 5: The connector of clause 4, wherein the stopping mechanism includes two ledges disposed diametrically opposite each other.

Clause 6: The connector of clause 1, wherein the retaining mechanism includes one or more barbed features projecting radially inward from the inner circumferential surface.

Clause 7: The connector of clause 4, wherein the retaining mechanism includes two barbed features disposed diametrically opposite each other.

Clause 8: An assembly, comprising: a connector comprising: a body having a tubing portion and a luer portion axially opposite the tubing portion and connected thereto, an internal passageway defined by an inner circumferential surface of the connector, the passageway extending axially between the tubing portion and the luer portion and in fluid communication therewith, a stopping mechanism disposed in the luer portion and configured to limit an extent of a fluid line disposed in the connector, and a retaining mechanism disposed in the tubing portion and configured to retain the fluid line in the connector; a first core pin comprising: a first core pin body having a first base portion and a luer-shaping portion connected to each other, wherein two ledge-forming profiles are defined at a distal end of the first core pin and disposed diametrically opposite each other; and a second core pin comprising: a second core pin body having a second base portion and a tubing-shaping portion connected to each other, wherein a barb-forming profile is defined at a distal end of the second core pin.

Clause 9: The assembly of clause 8, wherein each ledge-forming profile includes a first planar surface and a second planar surface, each formed on an outer surface of the first core pin, the first planar surface extends axially a first distance and at a first angle with respect to the axis of the assembly, and the second planar surface extends axially a second distance from the first planar surface to the distal end and at a second angle with respect to the axis of the assembly, the first angle and the second angle being different.

Clause 10: The assembly of clause 8, wherein the barb-forming profile includes: two axially extending prongs and a cavity defined therebetween, the cavity being defined by a planar bottom surface of the core pin disposed perpendicular to the axis of the assembly at the distal end of the second core pin and an angled inner surface of each prong, and two chamfered edges disposed diametrically opposite each other, each chamfered edge being defined between the planar bottom surface and an outer surface of the second core pin.

Clause 11: The assembly of clause 8, wherein the ledge-forming profiles and the barb-forming profile cooperatively form the stopping mechanism and the retaining mechanism.

Clause 12: The assembly of clause 8, wherein the luer-shaping portion at least partially defines the luer portion of the connector and the tube-shaping portion at least partially defines the tubing portion of the connector.

Clause 13: A method of manufacturing a connector, comprising: providing a first core pin and a second core pin, the first core pin comprising: a first core pin body having a first base portion and a luer-shaping portion connected to each other, wherein two ledge-forming profiles are defined at a distal end of the first core pin and disposed diametrically opposite each other, and the second core pin comprising: a second core pin body having a second base portion and a tubing-shaping portion connected to each other, wherein a barb-forming profile is defined at a distal end of the second core pin; inserting the first and second core pins into a material forming the connector, the first and second core pins being axially aligned and inserted into the material from opposite ends; and contacting the distal ends of the first and second core pins with each other such that the ledge-forming profiles are at least partially received into the barb-forming profile.

Clause 14: The method of clause 13, wherein contacting the distal ends of the first and second core pins forms the connector comprising: a tubing portion and a luer portion axially opposite the tubing portion and connected thereto, an internal passageway defined by an inner circumferential surface of the connector, the passageway extending axially between the tubing portion and the luer portion and in fluid communication therewith, a stopping mechanism disposed in the luer portion and configured to limit an extent of a fluid line disposed in the connector, and a retaining mechanism disposed in the tubing portion and configured to retain the fluid line in the connector.

Clause 15: The method of clause 14, wherein each ledge-forming profile includes a first planar surface and a second planar surface, each formed on an outer surface of the first core pin, the first planar surface extends axially a first distance and at a first angle with respect to the axis of the assembly, and the second planar surface extends axially a second distance from the first planar surface to the distal end and at a second angle with respect to the axis of the assembly, the first angle and the second angle being different.

Clause 16: The method of clause 14, wherein the barb-forming profile includes: two axially extending prongs and a cavity defined therebetween, the cavity being defined by a planar bottom surface of the core pin disposed perpendicular to the axis of the assembly at the distal end of the second core pin and an angled inner surface of each prong, and two chamfered edges disposed diametrically opposite each other, each chamfered edge being defined between the planar bottom surface and an outer surface of the second core pin.

Clause 17: A connector, comprising: a tubular having a first port at a first axial end; an internal passageway defined in the tubular, the first port fluidly communicating with the internal passageway; a first barbed feature disposed adjacent the first axial end and on an outer circumferential surface of the tubular, the first barbed feature protruding radially away from the outer circumferential surface; a first collar disposed about at least a portion of the tubular adjacent the first axial end and radially spaced from the tubular, the first collar and the outer circumferential surface of the tubular defining a first gap therebetween; a second collar connected to the outer circumferential surface of the tubular and connected to the first collar, a first opening being defined between the second collar and the first collar; and a plurality of first ribs arranged circumferentially spaced from each other on an inner circumferential surface of the first collar, wherein each first rib at least partially defines a first edge with an inner circular end face of the first collar, and wherein the first edge protrudes into the first gap.

Clause 18: The connector of claim 17, wherein the tubular has a second port at a second axial end opposite the first axial end and the internal passageway fluidly connects the first port with the second port, and the connector further comprises: a second barbed feature disposed adjacent the second axial end and on an outer circumferential surface of the tubular, the second barbed feature protruding radially away from the outer circumferential surface; a third collar disposed about at least a portion of the tubular adjacent the second axial end and radially spaced from the tubular, wherein the third collar and the outer circumferential surface of the tubular define a second gap therebetween, and the third collar is connected to the second collar and a second opening is defined therebetween; and a plurality of second ribs arranged circumferentially spaced from each other on an inner circumferential surface of the third collar, wherein each second rib at least partially defines a second edge with an inner circular end face of the third collar, and wherein the second edge protrudes into the second gap.

Clause 19: The connector of claim 17, wherein each first edge and first barbed feature are axially aligned with each other.

Clause 20: The connector of claim 17, wherein each first edge and first barbed feature are axially offset from each other.

Clause 21: The connector of claim 17, wherein each second edge and second barbed feature are axially aligned with each other.

Clause 22: The connector of claim 17, wherein each second edge and second barbed feature are axially offset from each other.

Clause 23: The connector of claim 17, further comprising a fluid line inserted over the first barbed feature, wherein the first edges of the first ribs contact an outer surface of the fluid line.

Clause 24: The connector of claim 17, wherein the outer circumferential surface of the tubular includes a luer profile.

Clause 25: The connector of claim 17, wherein the tubular has a second axial end opposite the first axial end, and the second collar is disposed around at least a portion of the tubular adjacent the second axial end.

Clause 26: The connector of claim 25, wherein the second collar includes a plurality of protrusions disposed extending radially inward from an inner circumferential surface of the second collar, the plurality of protrusions being axially spaced from each other.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:
1. A connector, comprising:
a body having a tubing portion and a luer portion axially opposite the tubing portion and connected thereto;
an internal passageway defined by an inner circumferential surface of the connector, the internal passageway extending axially between the tubing portion and the luer portion and in fluid communication therewith;
a stopping mechanism comprising one or more discontinuous ledges projecting from the inner circumferential surface along the luer portion in a direction that is radially inward into the internal passageway and configured to limit an extent of a fluid line disposed in the connector; and a retaining mechanism projecting from the inner circumferential surface along the tubing portion in a direction that is radially inward into the internal passageway, wherein the retaining mechanism is spaced apart from the stopping mechanism along an axis defined by the internal passageway and is offset from the stopping mechanism along a circumference around the axis, and configured to retain the fluid line in the connector.

2. The connector of claim 1, wherein the inner circumferential surface includes a tubing profile in the tubing portion and a luer profile in the luer portion.

3. The connector of claim 1, wherein the tubing portion includes a tubing port configured to receive a fluid line and the luer portion includes a luer port configured to receive a male luer connector, the tubing port and the luer port being in fluid communication through the internal passageway.

4. The connector of claim 1, wherein the one or more discontinuous ledges comprise two ledges disposed diametrically opposite each other.

5. The connector of claim 1, wherein the retaining mechanism includes two barbed features disposed diametrically opposite each other.

6. The connector of claim 1, wherein the retaining mechanism includes one or more barbed features projecting radially inward from the inner circumferential surface.

7. A method of manufacturing a connector, comprising:
providing a first core pin and a second core pin, the first core pin comprising:
   a first core pin body having a first base portion and a luer-shaping portion connected to each other, wherein two ledge-forming profiles are defined at a distal end of the first core pin and disposed diametrically opposite each other, and the second core pin comprising:
   a second core pin body having a second base portion and a tubing-shaping portion connected to each other, wherein a barb-forming profile is defined at a distal end of the second core pin;
inserting the first and second core pins into a material forming the connector, the first and second core pins being axially aligned and inserted into the material from opposite ends;
contacting the distal ends of the first and second core pins with each other such that the ledge-forming profiles are at least partially received into the barb-forming profile; and
forming a connector around outer surfaces of the first and second core pins, wherein the connector comprises:
   inner circumferential surface forming an internal passageway having a tubing portion and a luer portion, and defining an axis therethrough;
a stopping mechanism comprising one or more one or more discontinuous ledges projecting from the inner circumferential surface in a direction that is radially inward into the internal passageway; and a retaining mechanism projecting from the inner circumferential surface in a direction that is radially inward into the internal passageway, wherein the retaining mechanism is spaced apart from the stopping mechanism along the axis and is offset from the stopping mechanism along a circumference around an axis defined by the internal passageway.

8. The method of claim 7, wherein each ledge-forming profile includes a first planar surface and a second planar surface, each formed on an outer surface of the first core pin,
the first planar surface extends axially a first distance and at a first angle with respect to the axis of the connector, and
the second planar surface extends axially a second distance from the first planar surface to the distal end and at a second angle with respect to the axis of the connector, the first angle and the second angle being different.

9. The method of claim 7, wherein the barb-forming profile includes:
two axially extending prongs and a cavity defined therebetween, the cavity being defined by a planar bottom surface of the first core pin disposed perpendicular to the axis of the connector at the distal end of the second core pin and an angled inner surface of each prong, and
two chamfered edges disposed diametrically opposite each other, each chamfered edge being defined between the planar bottom surface and an outer surface of the second core pin.

\* \* \* \* \*